United States Patent
Fischer et al.

(10) Patent No.: US 6,365,762 B1
(45) Date of Patent: Apr. 2, 2002

(54) METHOD FOR CATALYTIC AND SELECTIVE OXIDATION OF AROMATIC COMPOUNDS

(75) Inventors: Richard Walter Fischer, Bad Soden; Joachim Haider, München; Wolfgang Anton Herrmann, Freising; Roland Kratzer, Kriftel, all of (DE)

(73) Assignee: Aventis Research & Technologies GmbH & Co. KG, Frankfurt (DE)

( * ) Notice: Subject to any disclaimer, the term of this patent is extended or adjusted under 35 U.S.C. 154(b) by 0 days.

(21) Appl. No.: 09/403,461

(22) PCT Filed: Mar. 31, 1998

(86) PCT No.: PCT/EP98/01864
§ 371 Date: Mar. 14, 2000
§ 102(e) Date: Mar. 14, 2000

(87) PCT Pub. No.: WO98/47837
PCT Pub. Date: Oct. 29, 1998

(30) Foreign Application Priority Data

Apr. 24, 1997 (DE) .......................... 197 17 176

(51) Int. Cl.$^7$ .......................... C07C 50/12; C07C 37/00; C07F 13/00; B01J 31/00
(52) U.S. Cl. .................. 552/296; 552/299; 568/741; 502/167; 556/47
(58) Field of Search .................. 552/296, 299; 568/741; 502/167; 556/47

(56) References Cited

U.S. PATENT DOCUMENTS 5,616,734 A    4/1997    Hermann et al. ............ 549/406
5,710,292 A    1/1998    Herrmann et al. .......... 552/296

OTHER PUBLICATIONS

Adam et al., Angew, Chem. Int. Ed. Engl. 1994, 33, No. 23/24.

Primary Examiner—Porfirio Nazario-Gonzalez
(74) Attorney, Agent, or Firm—Frommer Lawrence & Haug LLP

(57) ABSTRACT

The invention relates to the use of compounds of the formula $$R^1{}_a Re_b O_c L_d \qquad (I),$$

in which a = zero or an integer from 0 to 6
b = an integer from 1 to 4
c = an integer from 1 to 12
d = an integer from 0 to 4
L = Lewis base and the total of a, b and c is such as to comply with the pentavalency or heptavalency of rhenium, with the proviso that c is not larger than 3×b, and in which $R^1$ is absent or identical or different, and is an aliphatic hydrocarbon radical having 1 to 10 carbon atoms, an aromatic hydrocarbon radical having 6 to 10 carbon atoms or an arylalkyl radical having 7 to 9 carbon atoms, it being possible for the $R^1$ radicals where appropriate to be substituted identically or differently, independently of one another, as catalysts for oxidizing electron-rich aromatic compounds and their derivatives, the catalysts being employed in a peroxide-containing solution in the presence of an anhydride of a carboxylic acid and/or of a dehydrating agent.

11 Claims, No Drawings

METHOD FOR CATALYTIC AND SELECTIVE OXIDATION OF AROMATIC COMPOUNDS

The present invention relates to the use of Re catalyst systems for the oxidation of electron-rich aromatic compounds, the catalyst system having not only an extended useful life but also excellent activity, and to a process for the oxidation of electron-rich aromatic compounds using this catalyst system.

Oxidative processes play a crucial part in organic synthesis. Numerous basic and fine chemicals are prepared using atmospheric oxygen, hydrogen peroxide and alkyl peroxides. In most cases, the reactions are efficient and selective only if the oxidizing agents are used in the presence of catalysts. In practice, these are mostly metal oxides such as, for example, $V_2O_5$, $CrO_3$, $MoO_3$, $WO_3$, $OsO_4$ and $RuO_4$, which are employed, for example, in epoxidation, hydroxylation or carboxylation reactions (Catalytic Oxidations with Hydrogen Peroxide as Oxidant (Ed.: G. Strukul), Kiuwer, Dordrecht, 1992, 13–43; H. A. Jørgensen, Chem. Rev. 1989, Vol. 98, pp. 431–458).

Application of such systems to the catalytic oxidation of aromatic compounds is not self-evident: lack of activity ($WO_3$) on the one hand, deficient selectivity on the other hand ($CrO_3/H_2SO_4$), tendency to catalytic decomposition of hydrogen peroxide ($RuCl_3$), besides the frequent lack of acceptability in ecological and health terms (for example in the case of $OsO_4$ or $CrO_3$), which result in complicated and costly disposal, have to date prevented the use of such catalysts.

Other processes already established in oxidation chemistry and employing, for example, electrochemical oxidation, cerium(IV) salts, manganese(III) sulfate or peroxides (tBuOOH) in the presence of molybdenum complexes as oxidizing agents prove in the oxidation of simple or fused aromatic compounds and their derivatives to be complicated and costly, and are often associated, owing to the need to employ stoichiometric amounts (cerium(IV) salts, manganese(III) sulfate), with high salt burdens and are usually also nonspecific (R. P. Kreh et al., J. Org. Chem., 1989, 54, 1526–1531; M. Hudlicky, Oxidations in Organic Chemistry, ACS Monograph 186, Washington D.C. 1990, pp. 92–98; T. A. Gorodetskaya et al. U.S.S.R. Patent 1 121 255, 1984; Chem. Abstr., 1985, 102, 203754; W. Adam et. al., Synthesis, 1993, 280–282, J. Skarzewski, Tetrahedron, 1984, 40, 4997–5000; S. Yamaguchi et al., Bull. Chem. Soc. Jpn. 1986, 59, 2881–2884; M. Perisamy, M. V. Bhatt, Tetrahedron Lett. 1978, 4561–4562, Y. Asakawa et al., 1988, J. Org. Chem., 53, 5452–5457; W. Chen, Chem. Abstr., 1987, 107, 58620).

EP 0665209 A1 and EP 0686618 A1 disclose organorhenium compounds of the general type $R^1{}_aRe_bO_c.L_d$ (L=Lewis base) which are employed as catalysts for oxidizing a large number of aromatic compounds to quinoid systems in the presence of hydrogen peroxide.

These rhenium compounds can be synthesized in a simple manner from commercially available $Re_2O_7$ with the aid of conventional substances which act as donors of organic groups, for example in the case of $R^1=CH_3$ by reaction with commercially available tetramethyltin or commercially available dimethylzinc. They are insensitive to air and moisture, can be stored at room temperature and are, in conjunction with peroxide-containing compounds such as, for example, hydrogen peroxide, suitable catalysts for oxidizing aromatic compounds. However, it has emerged that the useful life of the catalysts, especially at the elevated temperature which is normally necessary, is only inadequate.

The object therefore was to find a catalyst system which is, where possible, easily obtainable, low-cost, simple to handle, storable and effective and which, besides high selectivity in the oxidation of aromatic compounds, shows improved useful life of the catalyst and excellent activity.

It has now been found, surprisingly, that on addition of anhydrides of carboxylic acids to the reaction system in combination with peroxide-containing compounds there is a drastic increase in the catalytic activity of rhenium compounds. This results in a decisive improvement in the previously disclosed process and was by no means to be expected.

The invention therefore relates to the use of compounds of the formula $$R^1{}_aRe_bO_c.L_d \qquad (I),$$

in which a = zero or an integer from 0 to 6
b = an integer from 1 to 4
c = an integer from 1 to 12
d = an integer from 0 to 4
L = Lewis base and the total of a, b and c is such as to comply with the pentavalency or heptavalency of rhenium, with the proviso that c is not larger than 3×b, and in which $R^1$ is absent or identical or different, and is an aliphatic hydrocarbon radical having 1 to 20 and preferably from 1 to 10 carbon atoms, an aromatic hydrocarbon radical having 6 to 20 and preferably from 6 to 10 carbon atoms or an arylalkyl radical having 7 to 20 and preferably from 7 to 9 carbon atoms, it being possible for the $R^1$ radicals where appropriate to be substituted identically or differently, independently of one another, and in the case of δ-bonded radicals at least one hydrogen atom is still bonded to the carbon atom in the α position, as catalysts for oxidizing electron-rich aromatic compounds and their derivatives in the presence of an anhydride of a carboxylic acid and of a peroxide-containing compound.

The invention further relates to a process for the oxidation of electron-rich aromatic compounds, which comprises oxidizing electron-rich $C_6$–$C_{22}$-aryl compounds and their derivatives in the presence of a catalyst of the formula $R^1{}_aRe_bO_c.L_d$ (I), in which $R^1$, a, b, c, d and L have the abovementioned meaning, of a peroxide-containing compound and of an anhydride of a carboxylic acid.

The compounds of the formula (I) can also be in the form of their Lewis base adducts. Typical examples of Lewis bases are pyridine, bipyridine, t-butylpyridine, amines, in particular secondary and tertiary amines such as triethylamine and quinuclidine, $H_2O$ and polyethers such as, for example, diglyme.

An aliphatic hydrocarbon radical $R^1$ means alkyl radicals having 1 to 20 and preferably from 1 to 10 carbon atoms, alkenyl or alkynyl radicals having 2 to 20 and preferably from 2 to 10 carbon atoms, cycloalkyl or cycloalkenyl radicals having 3 to 20 and preferably from 3 to 10 carbon atoms. Suitable examples of $R^1$ are alkyl radicals such as methyl, ethyl, propyl, isopropyl and the various butyl, pentyl, hexyl, octyl radicals such as ethylhexyl and decyl radicals, and alkenyl radicals such as allyl; also suitable are cycloalkyl radicals such as cyclopropyl, cyclobutyl, cyclopentyl, alkylated cyclohexyl such as hydrogenated tolyl, xylyl, ethylphenyl, cumyl or cymyl, 1-menthyl and 1-norbonyl, and alkenyl radicals such as vinyl and allyl and cycloalkenyl radicals such as cyclopentadienyl and pentamethylcyclopentadienyl.

Suitable examples of an aromatic hydrocarbon radical $R^1$ are phenyl or naphthyl. Benzyl may be mentioned as an example of an arylalkyl radical.

The radical $R^1$ can also be substituted. Examples of suitable substituents are fluorine, chlorine, bromine, $NH_2$, $NR^2_2$, $PH_2$, $PHR^2$, $PR^2_2$, OH or $OR^2$, where $R^2$ is identical or different and is an alkyl radical having 1 to 20 and preferably from 1 to 10 carbon atoms or an aryl radical having 6 to 20 and preferably from 6 to 10 carbon atoms, which may, for example, have the meanings stated above for $R^1$.

Very particularly preferred compounds of the formula (I) are the rhenium oxides methylrhenium trioxide ($CH_3ReO_3$), cyclopentadienylrhenium trioxide ($CpReO_3$), cyclopropylrhenium trioxide ($C_3H_5ReO_3$) and dirhenium heptoxide ($Re_2O_7$).

It is essential to the invention that the reaction system comprises an anhydride of a carboxylic acid.

Particularly suitable anhydrides for the present invention are those of aliphatic carboxylic acids, with anhydrides of aliphatic carboxylic acids having 1–6 carbon atoms being preferred, and it also being possible for the carboxylic acid to be unsaturated and/or branched.

Suitable examples are, in particular, the anhydrides of acetic acid, propionic acid, n-butyric acid, n-valeric acid, n-caproic acid, i-butyric acid, i-valeric acid, ethylmethylacetic acid, trimethylacetic acid, propenoic acid, methacrylic acid, crotonic acid and vinylacetic acid.

The amount of anhydride to be added is not critical but a mixing ratio of anhydride to solvent of from 1:10 to 10:1 has proven suitable.

It is possible to use organic solvents as liquid medium for the reaction system.

Examples of suitable solvents are the anhydride itself, a carboxylic ester such as ethyl acetate, a carboxylic acid, alcohols having 1–5 carbon atoms such as methanol, ethanol and the various propanols and butanols, with tert-butanol being particularly preferred, aromatic hydrocarbons such as toluene, ethers such as diethyl ether, di-n-butyl ether, tert-butyl methyl ether, aliphatic hydrocarbons such as hexane, heptane, methylene chloride, tetrahydrofuran and acetonitrile, and mixtures thereof.

It is preferred according to the invention to use a carboxylic acid, in particular the carboxylic acid corresponding to the anhydride.

It is preferred to use a combination of carboxylic acids and their anhydrides of the formula (II)

and

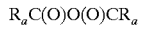 (II)

where $R_a$ is an aliphatic hydrocarbon radical having 1 to 10 and preferably from 1 to 5 carbon atoms.

Examples of suitable representatives are the same as those mentioned above.

Because it is easily available, acetic acid (glacial acetic acid) and its anhydride are particularly preferred.

The added anhydride may in this case perform several functions: it may on the one hand act as precursor for peracid, and on the other hand as dehydrating agent to trap water from the reaction solution. The hydrolysis product is moreover, in the preferred case, identical to the carboxylic acid employed and facilitates subsequent working up of the reaction solution, because it is unnecessary to employ any salt-containing and, in particular, halogen-containing desiccants which must subsequently be removed, possibly with difficulty, from the product.

The anhydride employed is, just like, for example, acetic acid and hydrogen peroxide, a low-cost bulk chemical and provides a distinct saving in costs compared with the previous process, especially in view of the fact that the content of costly rhenium-based catalysts can be reduced by 50–75%. In addition, besides the increase in reactivity, there is found to be an increase in the selectivity to as much as 92% based on the starting material employed.

It has emerged that the useful life of the catalysts can be increased further in particular under conditions which are as anhydrous as possible.

In another embodiment of the invention, the water of reaction can also be removed from the reaction system by adding dehydrating agents. It is then possible in this case to dispense with the use of the anhydride. However, it is also possible to employ the anhydride and the dehydrating agent together. Conventional organic and inorganic dehydrating agents can be used for the present invention as long as they are compatible with the peroxide-containing compound.

Examples thereof are $MgSO_4$, $Na_2SO_4$, $CaCl_2$, $H_2SO_4$ and orthoesters of carboxylic acids.

The amount of dehydrating agent to be added depends on its water-absorbing capacity and is in general from 0.05 to 10 mole equivalents based on the amount of peroxide-containing compound.

Aryl compounds suitable for the process according to the invention are electron-rich aromatic compounds or fused aromatic systems having 6 to 22 carbon atoms, preferably having 6 to 14 carbon atoms, which may, where appropriate, be substituted one or more times, identically or differently by an electron donor group. Typical suitable electron donor groups are hydroxyl, $C_1$–$C_3$-alkoxy, N-acylamino-, N-acylamino-$C_1$–$C_3$-alkyl, acyloxy and $C_1$–$C_3$-alkyl radicals.

Examples of such aryl compounds are xylenes, di-, tri- or tetrasubstituted $C_1$–$C_3$-alkylbenzenes or $C_1$–$C_3$-alkoxybenzenes, and, in particular, naphthalene and its $C_1$–$C_3$-alkyl or $C_1$–$C_3$-alkoxy derivatives substituted once to six times, anthracene and its $C_1$–$C_3$-alkyl or $C_1$–$C_3$-alkoxy derivatives, phenanthrene and more extensively fused aromatic compounds, phenols, hydroquinone, resorcinol, catechol and pyrrogallol, but also biphenyl.

Preferred aryl compounds are naphthalene and anthracene, and their derivatives, and naphthalene and its derivatives are particularly preferred, especially 2-methylnapthalene.

The process according to the invention generally results in the aryl compounds being oxidized to the corresponding quinoid systems. For example, 2-methylnaphthalene results in 2-methyl-1,4-naphthoquinone, which is the basis of the vitamin K series.

In the case of aryl compounds with more substituents (three or more), where the formation of a quinoid system is impossible, the process according to the invention results in preparation of the corresponding hydroxyl compound. Typical examples of such aryl compounds with more substituents are 1,2,3,5,8-pentamethylnaphthalene; 1,2,3-trimethylbenzene, mesitylene and 1,3,5-trimethoxybenzene. These starting materials afford by the process according to the invention, for example, the following hydroxyl compounds: 4-hydroxy-1,2,3,5,8-pentamethylnaphthalene and 1-hydroxy-2,4,6-trimethoxybenzene.

Examples of suitable peroxide-containing compounds are hydrogen peroxide, inorganic peroxides, for example alkali metal peroxides such as sodium peroxide, and percarboxylic acids and their salts such as, for example, m-chlorobenzoic acid, peracetic acid and magnesium monoperoxophthalate, with hydrogen peroxide being particularly preferred because of its ready availability.

In the process according to the invention, the aromatic compound to be oxidized is dissolved in the organic solvent mixture described; and the catalyst is added.

The concentration of dissolved aromatic compound based on the solvent is 0.1 mol/l–10 mol/l, preferably 0.4 mol/l–4 mol/l and particularly preferably 0.5 mol/l–2 mol/l.

The catalyst can be employed in an amount of 0.01–10 mole percent, preferably 0.02–2 mole percent (Re metal catalyst based on the compound to be oxidized). The peroxide-containing compound (5–90 percent by weight) is normally added to this solution in a molar ratio of from 1:1 to 20:1 based on the compounds to be oxidized.

The reaction mixture is stirred at a temperature of, normally, 10–100° C., preferably 20–60° C., until conversion is complete. The reaction mixture is then worked up in a manner which is usual for the skilled worker, i.e. for example neutralized, extracted and dried. The crude extracted product can be further purified, for example, by high vacuum distillation or recrystallization.

The rhenium compounds of the formula (I) are compounds commercially obtainable by purchase ($Re_2O_7$) or can easily be prepared (G. Brauer, Handbuch der Präparativen Anorganischen Chemie [Handbook of preparative inorganic chemistry], 3rd edition, Enke-Verlag, Stuttgart 1981, W. A. Herrmann, J. Organomet. Chem., 1995, 500, 149–174.).

Although their suitability in principle as oxidizing catalyst for aromatic compounds was known (EP 0665209 A1 and EP 0686618 A1), combining these catalysts with a peroxide-containing compound such as, for example, hydrogen peroxide and an anhydride of a carboxylic acid and/or from dehydrating agents is novel and results in a drastic increase in the catalytic activity, which was by no means to be expected because, in particular, the resistance to anhydrides of the rhenium compound used is surprising according to the current state of knowledge. The described invention thus represents a considerable advance by comparison with the previously disclosed processes, especially with regard to useful life, activity and selectivity, and is therefore of considerable significance in practice.

The following examples serve to illustrate the present invention.

EXAMPLES

General Method for the Rhenium-catalyzed Oxidation of Aromatic Compounds 1.00 g (7 mmol) of 2-methylnaphthalene is dissolved in a combination of 10 ml of glacial acetic acid and 5 ml of acetic anhydride in a reaction vessel maintained at the required temperature, and 0.5 to 1.0 mole percent of the appropriate catalyst is added. Finally, 1.4 ml of $H_2O_2$ (85 percent by weight) are added (aryl compound/$H_2O_2$ molar ratio: 1:7). The reaction is stirred at 40 or 60° C. for 4 h or longer (see table), ensuring exact maintenance of the temperature.

Workup

The reaction solution is neutralized with a saturated sodium bicarbonate solution, the aqueous mother liquor is extracted with methylene chloride, and the combined substrates are dried over $MgSO_4$. The solvent is removed in vacuo, resulting in 2-methyl-1,4-naphthoquinone as solid yellow oxidation product.

The method can be applied analogously to other aromatic compounds.

The examples carried out in accordance with the above method are to be found in Table 1.

Control experiments were carried out likewise in accordance with the above method but without addition of catalyst. Conversion at 40° C. after 4 h was only 13% at 40° C. and 60% at 60° C. with a selectivity of 17 and 25%, respectively, based on 2-methylnaphthalene (starting material).

TABLE 1

Compilation of oxidation examples

| No. | Catalyst | Concentration [mol %] | T [° C.] | t [h] | Conversion [%] | Selectivity[a] [%] |
|---|---|---|---|---|---|---|
| 1 | MTO | 0.5 | 40 | 1.3 | 46 | 55 |
| 2 | MTO | 1.0 | 40 | 4.0 | 74 | 54 |
| 3 | CpReO$_3$ | 0.5 | 40 | 4.0 | 60 | 66 |
| 4 | CpReO$_3$ | 1.0 | 40 | 4.9 | 71 | 68 |
| 5 | MTO | 0.5 | 60 | 3.5 | 89 | 75 |
| 6 | MTO | 1.0 | 60 | 2.5 | 87 | 92 |
| 7 | CpReO$_3$ | 0.5 | 60 | 1.5 | 75 | 85 |
| 8[b] | MTO | 2.0 | 40 | 4.0 | 56 | 61 |
| 9[b] | — | — | 40 | 4.0 | 13 | 17 |
| 10[b] | — | — | 60 | 4.0 | 60 | 25 |

MTO = Methyltrioxorhenium
CpReO$_3$ = Cyclopentadienyltrioxyrhenium
Solvent Nos. 1–8 = 10 ml of glaciai acetic acid plus 5 ml of acetic anhydride

[a] The selectivity is based on 2-methylnaphthalene (starting material)
[b] Control experiments:
Solvent No. 8 15 ml of glacial acetic acid (reference: W. Adam et al., Angew. Chem. 1994, 33, 2475–2476).
Solvent Nos. 9 and 10 Experiments carried out in accordance with the above method in the absence of catalyst Example 11 and Comparative Example 12

Oxidation of 2,3,5-trimethylbenzene (TMB) with and without Addition of Dehydrating Agent Composition of the Reaction Solution 50 mg MTO (0.2 mmol, 2 mol %)
1,2 g TMB (10 mmol)
2 ml $H_2O_2$ (85%, ca. 70 mmol)
in 20 ml acetic acid.

Working up was carried out by extraction with dichloromethane, washing with water, stripping off the solvent and purifying the resulting product on a silica gel column (pentane/EtOAc 5:1).

The following yields are obtained:

2 h/70° C.: 8%
2 h/70° C. and addition of 1.5 g of MgSO$_4$: 16%
4 h/40° C.: 8%
4 h/40° C. and addition of 1.5 g of MgSO$_4$: 11%.

What is claimed is:

1. A process for the oxidation of election-rich aromatic compounds, which comprises oxidizing one or more election-rich C$_6$–C$_{22}$-aryl compounds and their derivatives in a solution of an anhydride of a carboxylic acid and a carboxylic acid in the presence of a catalyst, wherein the catalyst has the formula:

$$R^1{}_a Re_b O_c \cdot L_d \quad (I),$$

in which a = zero or an integer from 0 to 6
    b = an integer from 1 to 4
    c = an integer from 1 to 12
    d = an integer from 0 to 4
    L = Lewis base and the total of a, b and c is such as to comply with the pentavalency or heptavalency of rhenium, with the proviso that c is not larger than 3×b, with the exception of Re$_2$O$_2$, in which R$^1$ is absent or identical or different, and is an aliphatic hydrocarbon radical having 1 to 10 carbon atoms, an aromatic hydrocarbon radical having 6 to 10 carbon atoms or an arylalkyl radical having 7 to 9 carbon atoms, wherein the R$^1$ radicals, where appropriate, are optionally substituted identically or differently, independently of one another, and in the case of δ-bonded radicals, at least one hydrogen atom is still bonded to the carbon atom in the α-position and wherein, the anhydride is of the formula $$R_a C(O)O(O)CR_a$$

and the carboxylic acid is of the formula $$R_a COOH$$

where

R$_a$ is an aliphatic hydrocarbon radical having 1 to 10 carbon atoms, and the mixing ratio of anhydride to carboxylic acid is from 1:10 to 10:1.

2. The process according to claim 1, where the catalyst is a compound of formula (I) wherein R$^1$ is a C$_1$–C$_3$ alkyl
    a is 1,
    b is 1, and
    c is 1.

3. The process according to claim 1, where the catalyst is a compound of formula (I) wherein R$^1$ is cyclopentadienyl or its methyl derivative
    a is 1,
    b is 1,
    c is 1, and
    d is O.

4. The process according to claim 1, wherein the peroxide-containing compound is hydrogen peroxide.

5. The process according to claim 1, wherein the electron-rich aryl compound is a C$_6$–C$_{24}$ aryl compound.

6. The process according to claim 1, wherein the electron-rich aryl compound is naphthalene or its derivatives.

7. The process according to claim 6, wherein the electron-rich aryl compound is a 2-methylnaphthaline.

8. The process according to claim 1, wherein the anhydride is acetic anhydride and the carboxylic acid is glacial acetic acid.

9. The process according to claim 1, wherein the oxidation is carried out at a temperature selected from the range of 10 to 100° C.

10. The process according to claim 1 which further comprises a dehydrating agent.

11. The process according to claim 10 wherein the dehydrating agent is MgSO$_4$, Na$_2$SO$_3$, CaCl$_2$, H$_2$SO, or an orthoester of a carboxylic acid.

* * * * *